United States Patent
Ding et al.

(10) Patent No.: US 10,869,901 B2
(45) Date of Patent: Dec. 22, 2020

(54) HYDROLYZED CHICKEN STERNAL CARTILAGE EXTRACT, METHOD FOR PRODUCING THE SAME AND USE THEREOF

(71) Applicant: INFINITUS (CHINA) COMPANY LTD., Guangdong (CN)

(72) Inventors: Liugang Ding, Guangdong (CN); Yong Zhou, Guangdong (CN); Zhongbao Yue, Guangdong (CN); Danlin He, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 0 days.

(21) Appl. No.: 16/355,858

(22) Filed: Mar. 18, 2019

(65) Prior Publication Data

US 2020/0108103 A1    Apr. 9, 2020

(30) Foreign Application Priority Data

Oct. 9, 2018  (CN) .......................... 2018 1 1171965

(51) Int. Cl.
| | |
|---|---|
| *A61K 36/00* | (2006.01) |
| *A61K 35/57* | (2015.01) |
| *A61P 19/02* | (2006.01) |
| *A23J 1/10* | (2006.01) |
| *A23J 3/34* | (2006.01) |

(52) U.S. Cl.
CPC ................ *A61K 35/57* (2013.01); *A23J 1/10* (2013.01); *A23J 3/342* (2013.01); *A61P 19/02* (2018.01); *A61K 2236/15* (2013.01); *A61K 2236/51* (2013.01); *A61K 2236/53* (2013.01)

(58) Field of Classification Search
CPC ...................................................... A61K 36/00
USPC ........................................................ 424/725
See application file for complete search history.

(56) References Cited

FOREIGN PATENT DOCUMENTS

| | | |
|---|---|---|
| CN | 101711591 A | 5/2010 |
| KR | 20070092941 A | 9/2007 |

OTHER PUBLICATIONS

First Office Action dated Apr. 16, 2020 for Chinese patent application No. 201811171965.1, English translation provided by Global Dossier.
Schmidt, M. M. et al.,"Collagen extraction process", International Food Research Journal 23(3): 913-922 (2016).
Liu Aiqing et al., "Analysis on industrial processing technology for type II collagen and technical indicators of collagen products",Meat Industry, Season2, p. 31-34.
Tang, Hebin, et al., The Dynamic Change of Pathological Indicators in Papain-Induced Rat Osteoarthritis, Journal of South-Central University for Nationalities( Nat. Sci. Edition), Dec. 2013, vol. 32 No. 4, pp. 41-45.

*Primary Examiner* — Michael V Meller
(74) *Attorney, Agent, or Firm* — Yue (Robert) Xu; Apex Attorneys at Law, LLP

(57) ABSTRACT

The present disclosure relates to pharmaceutical field, providing a hydrolyzed chicken sternal cartilage extract, method for producing the same and use thereof. The hydrolyzed chicken sternal cartilage extract has a type II collagen content of ≥50% and a chondroitin sulfate content of ≥20%. In China, a huge amount of livestock and poultry are consumed, and the total consumption almost reaches ¼ of the worldwide livestock and poultry consumption. Chicken sternal cartilage is one of the main by-products in broiler chicken processing. In the present disclosure, a hydrolyzed chicken sternal cartilage extract rich in type II collagen and chondroitin sulfate is obtained by using biological enzymatic hydrolysis technique. Experiments results show that the hydrolyzed chicken sternal cartilage extract produced by the present disclosure has a good anti-inflammatory effect and can be used to prepare medications for treating osteoarthritis.

5 Claims, 2 Drawing Sheets

(Left Knee Joint, Grade 0)  (Right Knee Joint, Grade 0)

(Left Knee Joint, Grade 3)  (Right Knee Joint, Grade 3)

(Left Knee Joint, Grade 2)   (Right Knee Joint, Grade 2)

(Left Knee Joint, Grade 2)   (Right Knee Joint, Grade 2)

HYDROLYZED CHICKEN STERNAL CARTILAGE EXTRACT, METHOD FOR PRODUCING THE SAME AND USE THEREOF

CROSS REFERENCE TO RELATED APPLICATIONS

This application claims the priority of Chinese Patent Application No. 201811171965.1, filed on Oct. 9, 2018, and the disclosures of which are hereby incorporated by reference.

FIELD

The present disclosure belongs to fields of pharmaceutical and nutritional supplement, specifically relates to a hydrolyzed chicken sternal cartilage extract, method for producing the same and use thereof, and especially use of the hydrolyzed chicken sternal cartilage extract for the manufacture of a medicament for treating osteoarthritis.

BACKGROUND

Osteoarthritis (OA) is a degenerative disease. It is characterized by damage of articular cartilage, reactive hyperplasia of joint edges and subchondral bone due to advancing age, obesity, overstrain trauma, joint congenital abnormalities, joint deformities and many other factors. It is also known as osteoarthrosis, degenerative arthritis, senile arthritis and hypertrophic arthritis. Its clinical manifestations are gradual onset of joint pain, tenderness, stiffness, joint swelling, limited mobility, joint deformity, etc. Major pathological changes of osteoarthritis are cartilage degeneration and loss, and reactive hyperostosis at joint edge ligament attachments and subchondral bone then osteophytes form, and therefore cause joint pain, stiff deformity and joint dysfunction. Clinically, osteoarthritis can be divided into two types, primary and secondary. Primary osteoarthritis refers to the joint lesions associated with ageing, instead of any other diseases, while secondary osteoarthritis is caused by injury, inflammation, genetics and metabolism, endocrine disorders, etc. The incidence of osteoarthritis increases with age, and is higher among women than men. According to the World Health Organization, osteoarthritis occurs in 50% people aged 50 years or older, and 80% people aged 55 years or older. The prevalence of osteoarthritis in China is proximately 10% of the general population, which is about 100 million people. In China, there were only more than 40 million patients with osteoarthritis in 1990, while in 2000, it reached 80 million, and the number of patients reached more than 100 million.

Currently, the drugs for osteoarthritis on the market mainly are non-steroidal drugs. Non-steroidal anti-inflammatory drugs (NSAIDs) refer to a class of drugs that do not contain glucocorticoids but having anti-inflammatory, antipyretic, and analgesic effects, such as aspirin, ibuprofen, naproxen. However, non-steroidal drugs are only used for pain relief in the treatment of osteoarthritis, which cannot completely prevent joint damage or deterioration of the condition. In addition, non-steroidal drugs have certain side effects, which are presented as being likely to cause vertigo, cognitive impairment, lethargy, liver and kidney allergy and sclerosis, nausea and increases in blood pressure.

SUMMARY

In view of above, an object of the present disclosure is to provide a hydrolyzed chicken sternal cartilage extract, a method for preparing the same and its use in the manufacture of a medicament for treating osteoarthritis, in view of the problems of the conventional arts.

In order to accomplish the object of the present disclosure, the following technical solutions are used in the present disclosure.

A hydrolyzed chicken sternal cartilage extract is provided, in which type II collagen content is ≥50% and chondroitin sulfate content is ≥20%.

The present disclosure also provides a method for producing a hydrolyzed chicken sternal cartilage extract, comprising grinding chicken sternal cartilage and adding water;

adjusting pH of the resultant to 7.0 and heating to 55° C.;

adding alkaline protease and flavourzyme for enzymatic hydrolysis;

after inactivating the enzymes, centrifuging and then collecting supernatant; and filtering the supernatant with cloth and collecting filtrate to obtain a solution of the hydrolyzed chicken sternal cartilage extract.

Wherein, preferably, the amount of added water is 2 to 3 times the mass of the chicken sternal cartilage.

Preferably, the amount of the added alkaline protease is 0.2% to 0.3% of the mass of the chicken sternal cartilage; and the amount of the added flavourzyme is 0.3% to 0.5% of the mass of the chicken sternal cartilage.

Preferably, the mass ratio of the alkaline protease to the flavourzyme is 1:1 to 5:3.

In some embodiments, the amount of the added alkaline protease is 0.2% of the mass of the chicken sternal cartilage, the amount of the added flavourzyme is 0.5% of the mass of the chicken sternal cartilage. In some embodiments, the amount of the added alkaline protease is 0.3% of the mass of the chicken sternal cartilage, the amount of the added flavourzyme is 0.3% of the mass of the chicken sternal cartilage.

Preferably, in the method for producing the hydrolyzed chicken sternal cartilage extract of the present disclosure, the enzymatic hydrolysis condition is performed at 55° C. for 3 hours.

After the enzymatic hydrolysis, alkaline protease and flavourzyme need to be inactivated. One ordinary skill in the art can perform the enzyme inactivation using methods known in the art. In some embodiments, specifically, the enzyme inactivation is performed at 95° C. for 15 minutes.

In the method for producing the hydrolyzed chicken sternal cartilage extract of the present disclosure, after inactivating the enzyme, the supernatant is collected via centrifugation and then filtered with cloth, and the filtrate is collected to obtain a solution of the hydrolyzed chicken sternal cartilage extract. Wherein, preferably, the centrifuging is performed at 8000 r/min for 15 minutes. Preferably, the filtering with cloth is performed by passing through 200 mesh cloth.

Further, the method for producing the present disclosure also comprises steps of concentrating and drying.

In some embodiments, the concentration and drying, specifically, the concentrating is vacuum concentration until solid content is about 40%, and drying is spray drying.

The present disclosure also provides a hydrolyzed chicken sternal cartilage extract produced by the above method.

In a specific embodiment of the present disclosure, the effects of the hydrolyzed chicken sternal cartilage extract on inhibiting the activity of MMP-1, the level of inflammatory factors in serum of mice with arthritis are detected, and the effects of the hydrolyzed chicken sternal cartilage extract on rats with osteoarthritis is observed through pathological assay (tissue section). The results show that the obtained hydrolyzed chicken sternal cartilage extract has pretty good inhibitory activity on MMP-1, and the efficiency can be more than 70%. The levels of inflammatory factors in serum of mice with arthritis were lower than those of model group, and the results of pathological assay (tissue section) also show significant improvement, indicating that the hydrolyzed chicken sternal cartilage extract of the present disclosure has a good anti-inflammatory effect. Therefore, the present disclosure also provides a use of the hydrolyzed chicken sternal cartilage extract in the manufacture of a medicament for treating osteoarthritis.

It is known from the technical solution above that, the present disclosure provides a hydrolyzed chicken sternal cartilage extract, method for producing the same and use thereof. In the hydrolyzed chicken sternal cartilage extract of the present disclosure, type II collagen content is ≥50% and chondroitin sulfate content is ≥20%. In China, a huge amount of livestock and poultry are consumed, and the total consumption almost reaches ¼ of the worldwide livestock and poultry consumption. Chicken sternal cartilage is one of the main by-products in broiler chicken processing. In the present disclosure, a hydrolyzed chicken sternal cartilage extract rich in type II collagen and chondroitin sulfate is obtained by using biological enzymatic hydrolysis technique. Experiments results show that the hydrolyzed chicken sternal cartilage extract produced by the present disclosure has a good anti-inflammatory effect and can be used to prepare medications for treating osteoarthritis. Therefore, the present disclosure can not only increase the added value of chicken sternal cartilage, but also widen the application range thereof, and has positive social impacts and broad market prospects.

BRIEF DESCRIPTION OF DRAWINGS

In order to illustrate the technical solutions in the embodiments of the present disclosure or the conventional arts more clearly, the drawings used for illustrating the examples or the conventional arts will be described briefly hereinafter.

DETAILED DESCRIPTION

Figure 1:
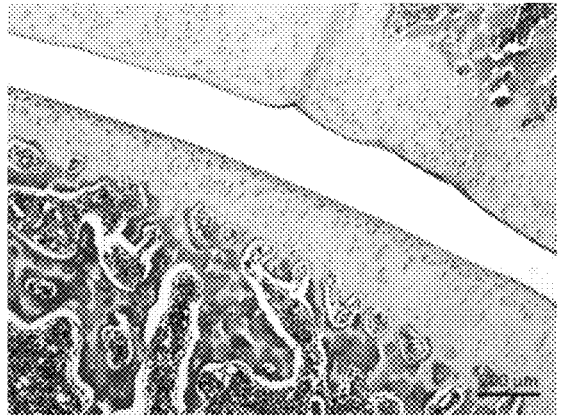
FIG. 1 shows knee joint sections of Normal Group.
Figure 1:
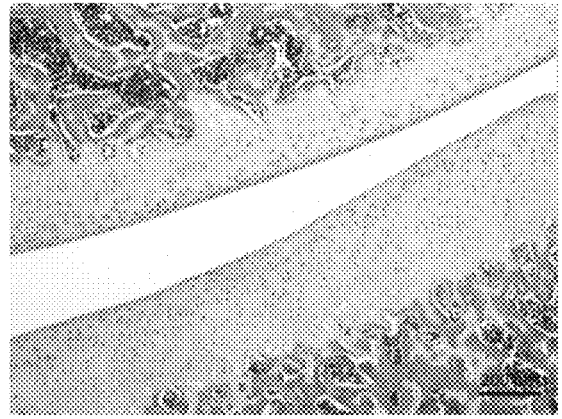

The present disclosure discloses a hydrolyzed chicken sternal cartilage extract, method for producing the same and use thereof. One ordinary skill in the art can learn from the contents of this disclosure and appropriately improve the process parameters to achieve the same invention. It is necessary to specially point out that all such alternatives and modifications are obvious to one ordinary skill in the art and are considered to be included in the present disclosure. The method and use of the present disclosure have been described in terms of preferred examples. It will be apparent to those ordinary skill in the art that the methods and applications described herein may be modified or modified and combined to implement and practice the techniques of the present disclosure without departing from the scope of the present disclosure.

In order to further understand the present disclosure, the technical solutions in the examples of the present disclosure will be described clearly and completely herein in conjunction with the examples of the present disclosure. Apparently, the described examples are only a part of the examples of the present disclosure, rather than all examples. Based on the examples in the present disclosure, all of other examples, made by one ordinary skill in the art without any creative efforts, fall into the protection scope of the present disclosure.

Unless otherwise stated, all the reagents in the examples of the present disclosure are commercial products, which can be purchased on the market.

EXAMPLE 1

A method for producing a hydrolyzed chicken sternal cartilage extract having anti-arthritic effect comprises the following steps:

(1) chicken sternal cartilage was washed, drained and grinded;

(2) water 2 times of the chicken sternal cartilage was added, the pH of the mixture was adjusted to 7.0, and the mixture was stirred in a water bath and heated to 55° C.; alkaline protease (Novozymes) was added at an amount of 0.2% the mass of the chicken sternal cartilage and flavourzyme (Novozymes) was added at an amount of 0.5% the mass of the chicken sternal cartilage; enzymatic hydrolysis was performed at 55° C. for 3 hours, and the mixture was heated at 95° C. for 15 minutes to inactivate the enzymes; the resultant was centrifuged at 8000 r/min for 15 minutes, and the supernatant was collected and then filtered by passing through 200 mesh cloth; and the filtrate was collected to give a solution of hydrolyzed chicken sternal cartilage extract;

(3) the solution of hydrolyzed chicken sternal cartilage extract was concentrated under vacuum until the solid content was about 40%, and then subjected to spray drying to obtain hydrolyzed chicken sternal cartilage extract -A (containing 57.46% of type II collagen and 21.29% of chondroitin sulfate).

EXAMPLE 2

A method for producing a hydrolyzed chicken sternal cartilage extract having anti-arthritic effect comprises the following steps:

(1) chicken sternal cartilage was washed, drained and grinded;

(2) water 3 times of the chicken sternal cartilage was added, the pH of the mixture was adjusted to 7.0, and the mixture was stirred in a water bath and heated to 55° C.; alkaline protease (Novozymes) was added at an amount of 0.3% the mass of the chicken sternal cartilage and flavourzyme (Novozymes) was added at an amount of 0.3% the mass of the chicken sternal cartilage; enzymatic hydrolysis was performed at 55° C. for 4 hours, and the mixture was heated at 95° C. for 15 minutes to inactivate the enzymes; the resultant was centrifuged at 8000 r/min for 15 minutes, and the supernatant was collected and then filtered by passing through 200 mesh cloth; and the filtrate was collected to give a solution of hydrolyzed chicken sternal cartilage extract;

(3) the solution of hydrolyzed chicken sternal cartilage extract was concentrated under vacuum until the solid content was about 40%, and then subjected to spray drying to obtain hydrolyzed chicken sternal cartilage extract -B (containing 54.83% of type II collagen and 22.08% of chondroitin sulfate).

EXPERIMENTAL EXAMPLE

1. Method (1) MMP-1 (Collagenase) Activity Inhibition Assay

Reagent Preparation:

Phosphate buffer: 1.4499 g of disodium hydrogen phosphate and 0.1482 g of sodium dihydrogen phosphate were weighed, and 500 mL of deionized water was added to make a solution of 5 mmol/L.

Collagenase solution: 30 mg of collagenase was weighed and 150 mL of the phosphate buffer was added.

Test Method:

A certain amount of insoluble collagen, as a substrate, was placed in 25 mL flask, and 5 mL of collagenase solution (0.2 mg/mL) was added; 0.2 mL of the hydrolyzed chicken sternal cartilage extract (10 mg/mL) obtained in each example was added as an enzyme inhibitor; 4.8 mL of PBS (5 mmol/L, pH=7.4) was added as a buffer, and collagen proteolysis reaction was carried out in a constant temperature incubator (37.0±0.1° C.) for 6 h with shaking to mix well; and then the resultant after enzymolysis was quickly filtered to obtain a clear filtrate; 2 mL of the filtrate was taken to measure the hydroxyproline content; the total hydroxyproline in the clear solution after enzymolysis ($Hyp_{Total}$) was calculated. The group without test sample was set as blank group, and the hydroxyproline content in the clear solution after enzymolysis was set as $Hyp_{Blank}$;

$$Hyp_{Inhibition} = Hyp_{Total} - Hyp_{Sample}$$

$$\text{Enzyme Inhibition Rate} = \left(1 - \frac{Hyp_{Inhibition}}{Hyp_{Blank}}\right) \times 100\%$$

In the equation, $Hyp_{Sample}$ is the hydroxyproline content in the group treated with the hydrolyzed chicken sternal cartilage extract.

(2) Verification Test in Rat Model (a) Rat Feeding and Management 50 healthy male Wistar rats of 300 g±10.0 g body weight were used. After the osteoarthritis model was established successfully, the rats were randomly divided into Sham Surgery Group (10 rats), Model Group (10 rats), Group A (10 rats) and Group B (10 rats). The rats were housed at temperature 20° C. to 26° C., humidity 40% to 70%, and the feed was provided by Guangdong Medical Laboratory Animal Center, Production License Number: SCXK (Yue) 2013-0002, Feed Quality Certificate Number: NO. 44200300015068. The rats were housed in a barrier animal facility. Laboratory Animal Use License Number: SYXK (Yue) 2014-0137.

The test samples were administered by oral gavage. Sample group: Group A, 100 mg/kg BW; Group B, 100 mg/kg BW; Sham Surgery Group and Model Control Group were given the same dose of pure water.

(b) Establishment of Osteoarthritis Rat Model

Under sterile conditions, 0.8000 g of papain was weighed and 16.0 mL of saline was added to prepare a solution with a concentration of 5%. The solution was stirred with a magnetic stirrer until homogeneous (would not clog the needles) and stored at 4° C. 4 hours before the experiment, the solution was taken out and returned to room temperature for use. The animals in Model Group were treated with 5% papain to establish osteoarthritis model.

Before the test, the rats were anesthetized by intraperitoneal injection of 3% pentobarbital sodium. Firstly, the hair in the 1 cm² area around the right knee joint was shaved, after disinfected with 75% ethanol, flexed 45° and the outer edge of the patellar tendon of the patella lower pole was the needle entry point, the needle was inserted to the direction of intercondylar fossa of femur, taken back 2 mm after reaching the femoral condyle, 150 µl of papain saline solution was injected into the right knee joint cavity to induce osteoarthritis. The same amount of sterile saline was injected to Sham Surgery Group. Injections were performed for model establishment respectively on the $1^{st}$ and $5^{th}$ test days. Seven days after the first injection, the animals in Model Group were randomly divided into Model Control Group, Group A and Group B, 10 rats in each group. The animals in each sample groups were given corresponding drugs according to administration volume at the dose of 10 mL/kg. Sham Surgery Group and Model Control Group were given the same amount of pure water by intragastric administration and continued for 30 days. (Tang Hebin et al., Journal of South-central University for Nationalities, Vol. 32, No.4, December 2013).

(c) Determination of Rat Serum Indicators

After 3% pentobarbital sodium was intraperitoneally injected for anesthesia, 5 mL of blood was collected from the abdominal aorta after the abdominal cavity was opened. After blood collection, the blood sample was left at room temperature for 2 hours, and then centrifuged at 3000 r/min for 15 minutes; the supernatant (serum) was collected and store at −80° C. Serum TNF-α, IL-1β and IL-10 were measured by a kit purchased from Luminex, serum IL-8 was measured by a kit purchased from Nanjing Jianjin, and serum MMP-13 was measured by a kit purchased from Wuhan Huamei.

(d) Pathological Observation of Rat Tissue Sections

Fixation: knee joints of the left and right hind limbs of the rats were taken and cut into tissue block of appropriate size, and then fixed in 4% formaldehyde solution for no less than 4 hours.

Decalcification Treatment: the rat joints after fixation were immersed in a decalcifying solution for 14 hours, and then rinsed with running water overnight.

Dehydration Treatment: the decalcified rat joint blocks were immersed in alcohol with gradient concentration of 80%, 95% and 100% successively, the immersion durations were 3 hours, 45 minutes and 30 minutes, respectively; wherein the immersion in 100% alcohol was performed twice, and the immersion durations were both 30 minutes. Then the rat joint blocks were immersed twice in xylene for 30 minutes each time.

Paraffin Embedding: firstly, a small amount of melted paraffin was poured into a embedding mold, and the embedding cassette was opened, preheated curved blunt tip tweezers were used to pick up the tissue block which had been partially immersed in wax, flatly placed in the center of the bottom surface of the embedding mold, then wax was added to cover the mold. After the surface of the melted wax in the embedded mold was solidified, it was transferred to a cold plate to accelerate solidification. Finally, the excess paraffin around the tissue block was removed with a blade or a trimming device.

Rough Cut: pre-cooled wax block was installed on the holder. The blade was installed on the holder and the position of the holder was adjusted so that the wax block could touch the blade. Then, the surface of the wax block was cut into slice (15~20 µm) by a rotating blade until the tissue block was completely shown out.

Fine Cut: the cutting wheel was adjusted for a cutting thickness of 3 to 5 µm. The wax section was attached to a microscope slide, and dried in the air. Then the microscope slide was placed on a slide dryer for drying, and then put into an oven for drying (60° C., 30 minutes). After the above steps, the section was ready for staining.

Dewaxing: the section was respectively placed in xylene I and xylene II and immersed for 5 to 10 minutes, then respectively placed in absolute ethanol I and absolute ethanol II and immersed for 1 to 3 minutes, then the section was placed in 95% ethanol I and 95% ethanol II and respectively immersed for 1 to 3 minutes, then the section was placed in 80% ethanol and immersed for 1 minute, and finally immersed in distilled water for 1 minute.

H & E Staining: firstly, the section was placed in hematoxylin solution and stained for 5 to 10 minutes, then the section was placed in distilled water and immersed for 1 minute, then immersed in 1% hydrochloric acid-ethanol solution for 1 to 3 second, then the section was placed in distilled water and immersed for 1 to 3 seconds, then the section was placed in warm water for 5 to 10 minutes for bluing, then stained with 0.1% eosin solution for 1 to 3 minutes, and finally rinsed with distilled water for 1 to 2 seconds, then removed quickly.

Dehydration: the section was respectively rinsed with 80% ethanol for 1 to 2 seconds and then respectively immersed in 95% ethanol I and 95% ethanol II for 2 to 3 minutes, then the section was collected out, placed in absolute ethanol I and absolute ethanol II and immersed for 3 to 5 minutes. Then the section was transferred to xylene I, xylene II, and xylene III and immersed for 3 to 5 minutes respectively.

Neutral Balata Mounting: a drop of neutral balata was added to the tissue section. One side of a cover slip was clamped with tweezers to make the cover slip touch the balata, the cover slip was lowered slowly to ensure there was no air bubble between the slides, and then the slides were dried in the air for 12 hours.

(e) Histopathology Semi-Quantitative Grading of Cartilage: the OOCHAS method established by the International Society for OA Research was used for semi-quantitative grading of cartilage histopathology: Grade 0, cartilage surface intact, complete cartilage; Grade 1, cartilage superficial fibrillation formation, and uneven; Grade 2, cartilage surface discontinuity, accompanied by cell proliferation, increased or decreased in Layer II to Layer III of metachromatic material; Grade 3, cartilage vertical fissures to Layer III or erosion occurrence; Grade 4, erosion aggravation, articular cartilage damage occurrence; Grade 5, articular cartilage denudation; Grade 6, joint deformation.

Statistical Analysis: all data were expressed as ($\bar{x} \pm s$) and processed by SPSS 16.0 statistical software. Differences between groups were compared by t test. $P<0.05$ was considered statistically significant.

2. Result (1) MMP-1 Activity Inhibition Assay

MMP-1, also known as collagenase, is a type of matrix metalloproteinase that degrades collagen at the joints, leading to loss of collagen and deterioration of arthritis, therefore, by inhibiting the activity of MMP-1, it can effectively alleviate the degradation of collagen and contribute to the repair of joints. The hydrolyzed chicken sternal cartilage extract prepared in each of the examples was used to test its effect of inhibiting MMP-1 activity, and the results are shown in Table 1.

TABLE 1

Inhibition of MMP-1 Activity by Examples In Vitro

|  | $Hyp_{Blank}$ (μg) | $Hyp_{Sample}$ (μg) | $Hyp_{Total}$ (μg) | MMP-1 Inhibition Rate (%) |
| --- | --- | --- | --- | --- |
| Hydrolyzed chicken sternal cartilage extract - A | 739.37 | 632.58 | 743.70 | 84.97 |
| Hydrolyzed chicken sternal cartilage extract - B | 739.37 | 705.33 | 909.51 | 72.38 |

It can be found from Table 1 that hydrolyzed chicken sternal cartilage extract -A and -B had good effect on MMP-1 activity inhibition, among which hydrolyzed chicken sternal cartilage extract -A had the best effect, reaching 84.97%.

(2) Effects on Serum Inflammatory Factor Levels in Mice with Arthritis

Serum interleukin-8 (IL-8), interleukin-10 (IL-10) and interleukin-1β (IL-1β) are inflammation-related monitoring factors in patients with osteoarthritis. Higher content indicates the disease is more severe. At the same time, as important mediators of inflammatory diseases, it can enhance inflammatory cell chemotaxis and induce cell proliferation, and plays an important role in anti-infection, immune response regulation and anti-tumor. TNF-α, full name tumor necrosis factor α, which induces the production of cytokines by stimulating macrophages, may induce inflammation in the body. The anti-inflammatory activity of the drug can be detected by detecting the expression of inflammatory factors in mice with arthritis. The hydrolyzed chicken sternal cartilage extract prepared in each of the examples was used to test its effect on serum inflammatory factor levels in mice with arthritis, and the results are shown in Table 2.

TABLE 2

Effect of hydrolyzed chicken sternal cartilage extract on the Levels of Serum Inflammatory Factors in Mice with Arthritis (±s)

| Group | IL-8 (ng/l) | IL-1β (pg/mL) | IL-10 (pg/mL) | TNF-α (pg/mL) |
| --- | --- | --- | --- | --- |
| Normal Group | 222.3 ± 28.13 | 16.326 ± 2.63 | 18.852 ± 1.96 | 142.038 ± 9.052 |
| Model Group | 248.75 ± 61.91 | 18.00 ± 1.97 | 20.22 ± 2.41 | 143.27 ± 12.91 |
| Group A | 223.74 ± 37.36 | 13.33 ± 0.97** | 12.36 ± 1.75** | 131.99 ± 8.66* |
| Group B | 181.94 ± 23.23* | 14.01 ± 2.17* | 14.38 ± 1.72** | 142.25 ± 11.17 |

Note:
Compared with Model Group
*p < 0.05,
**p < 0.01

It can be seen from Table 2 that all inflammatory factor levels in the serum of osteoarthritis mice in Normal Group, Group A and Group B were lower than those in Model Group, and the difference is significant, illustrating that hydrolyzed chicken sternal cartilage extract -A and hydrolyzed chicken sternal cartilage extract -B had good anti-inflammatory effects.

(3) Effects on Rats with Osteoarthritis

Figure 2:
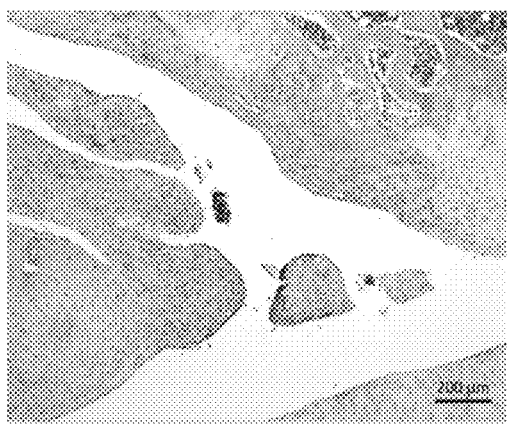
FIG. 2 shows knee joint sections of Model Group.
Figure 2:
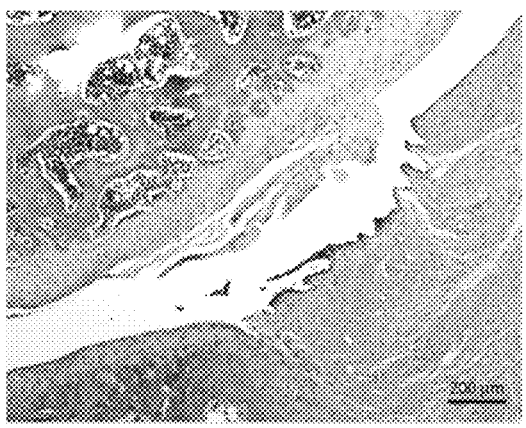
Figure 3:
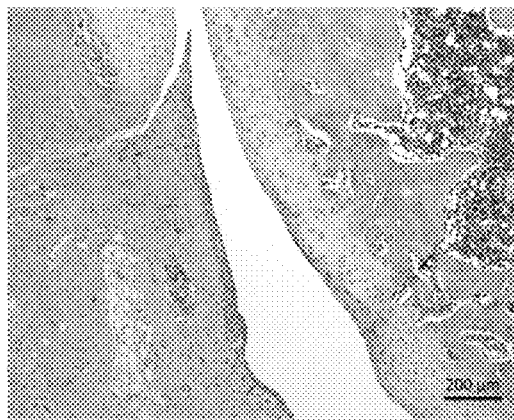
FIG. 3 shows knee joint sections of Group A treated with hydrolyzed chicken sternal cartilage extract -A.
Figure 3:
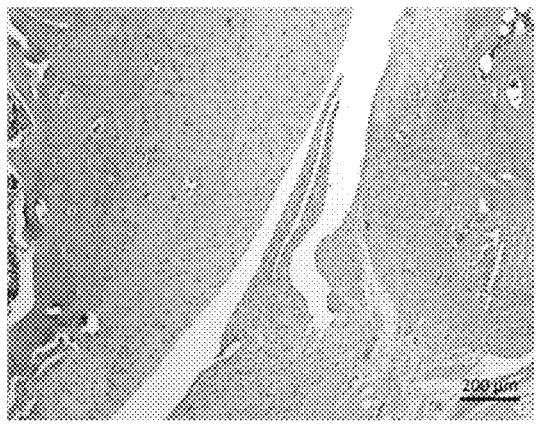
Figure 4:
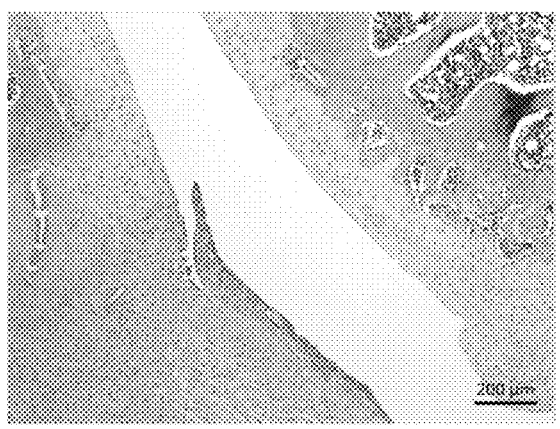
FIG. 4 shows knee joint sections of Group B treated with hydrolyzed chicken sternal cartilage extract -B.
Figure 4:
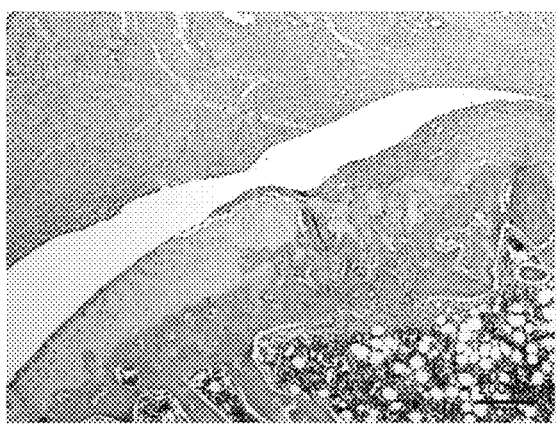

In the present disclosure, rat tissue sections were prepared and observed for pathological change to compare the effects of the hydrolyzed chicken sternal cartilage extract in each example on osteoarthritis in rats, and the results are shown in FIGS. 1-4.

From the pathological analysis in FIGS. 1-4, it can be seen that there was no obvious pathological abnormality in the left knee joint or the right knee joints of Sham Surgery Group. There were pathological abnormalities in the right knee joints of Model Group, hydrolyzed chicken sternal cartilage extract -A group (Group A) and hydrolyzed chicken sternal cartilage extract -B (Group B). The right knee joint of Model Group has the most complicated pathological changes, presenting as cartilage surface wear, surface fibrosis, abnormal arrangement of chondrocytes, joint synovial tissue hyperplasia, inflammatory cell infiltration, and pannus formation and went deep into the joint cavity. Compared with Model Group, there was only some superficial wear on the surface of the side of the knee articular cartilage in hydrolyzed chicken sternal cartilage extract -A Group and hydrolyzed chicken sternal cartilage extract -B Group; and some rats also had superficial fibrosis on the cartilage surface, but there were significant improvements in joint synovial tissue hyperplasia, inflammatory cell infiltration, and pannus formation compared with Model Group.

From the above analysis, it can be concluded that the hydrolyzed chicken sternal cartilage extracts A and B of the present disclosure all exhibit good effects on osteoarthritis.

The above are only preferred examples of the present disclosure, but the embodiments of the present invention are not limited to the above examples, any other changes, modifications, substitutions, combinations, and simplifications made without departing from the principles of the present disclosure should be considered as within the protection scope of the present disclosure.

What is claimed is:

1. A concentrated and spray dried hydrolyzed chicken sternal cartilage extract for treating osteoarthritis in a human in need thereof, which is produced by a method consisting essentially of the following steps:
   a) grinding chicken sternal cartilage and adding water to form a solution;
   b) adjusting the pH of the solution to 7.0 and heating the solution to 55° C.;
   c) adding an alkaline protease and an flavourzyme to the solution for enzymatic hydrolysis to form;
   d) after the enzymes are inactivated, centrifuging and then collecting supernatant of the solution;
   e) filtering the supernatant with a cloth and collecting the filtrate of the supernatant to obtain the hydrolyzed chicken sternal cartilage extract; and
   f) spray drying and vacuum concentrating the hydrolyzed chicken cartilage extract until the hydrolyzed chicken cartilage extract for treating osteoarthritis in a human in need thereof is formed;
   wherein the type II collagen content of the hydrolyzed chicken sternal cartilage extract is ≥50% and the chondroitin sulfate content of the hydrolyzed chicken cartilage extract is ≥20%.

2. The concentrated and spray dried hydrolyzed chicken sternal cartilage extract according to claim 1, wherein the amount of added water is 2 to 3 times the mass of the chicken sternal cartilage.

3. The concentrated and spray dried hydrolyzed chicken sternal cartilage extract according to claim 1, wherein the amount of added alkaline protease is 0.2% to 0.3% of the mass of the chicken sternal cartilage; and the amount of added flavourzyme is 0.3% to 0.5% of the mass of the chicken sternal cartilage.

4. The concentrated and spray dried hydrolyzed chicken sternal cartilage extract according to claim 1, wherein the mass ratio of the alkaline protease to the flavourzyme is 1 : 1 to 5 : 3.

5. The concentrated and spray dried hydrolyzed chicken sternal cartilage extract according to claim 1, wherein the enzymatic hydrolysis is performed at 55° C. for 3 hours; the inactivating of enzyme is performed at 95° C. for 15 minutes; the centrifuging is performed at 8000 r/min for 15 minutes; and the filtering is performed by passing through 200 mesh cloth.

* * * * *